United States Patent [19]
Henrick

[11] Patent Number: 5,151,443
[45] Date of Patent: Sep. 29, 1992

[54] METHOD OF CONTROLLING TERMITES

[75] Inventor: Clive A. Henrick, Palo Alto, Calif.

[73] Assignee: Sandoz Ltd., Basel, Switzerland

[21] Appl. No.: 823,574

[22] Filed: Jan. 16, 1992

Related U.S. Application Data

[63] Continuation of Ser. No. 556,492, Jul. 20, 1990, abandoned.

[51] Int. Cl.$^5$ ............................................. A01N 47/10
[52] U.S. Cl. ..................................... 514/486; 514/485
[58] Field of Search ................................ 514/486, 485

[56] References Cited

U.S. PATENT DOCUMENTS 4,968,829 11/1990 Henrick ................................ 558/289

FOREIGN PATENT DOCUMENTS 218543 4/1987 European Pat. Off. .

OTHER PUBLICATIONS

Haverty et al., Annals. Entomol. Soc. Am. 72.4, p. 503 ff; 1979.
Haverty et al.; J. Econ. Entomol. 82.5, 1370ff, 1989.
Jones; J. Econ. Entomol. 77.5, 1086H, 1984.
Mauldin et al.; Pest Control Technol. 13.3, 38 ff, 1985.
Nan-Yao et al.; J. Econ. Entomol. 78.6, 1259 ff, 1985.

Primary Examiner—Allen J. Robinson
Attorney, Agent, or Firm—Allen E. Norris

[57] ABSTRACT

A method of controlling termites employing substituted phenoxy, phenylthio and anilino compounds.

6 Claims, No Drawings

METHOD OF CONTROLLING TERMITES

This is a continuation of application Ser. No. 07/556,492, filed Jul. 20, 1990, now abandoned.

This invention relates to the use of substituted phenoxy, phenylthio and anilino compounds in controlling termites.

The control of termites is a problem faced in many countries of the world. Though various methods have been used with varying degrees of success, the still need exists for development of improved methods, allowing an effective and especially long-lasting control of termites. It has now been found that certain substituted phenoxy, phenylthio and anilino compounds are particularly effective in termite control.

The invention accordingly relates to a method of controlling termites which comprises applying to the termites or their locus or to a locus where protection against termite infestation is desired an effective amount of a compound of formula I.

$$R-(W^1)_m-\underset{Z}{\bigcirc}-(W)_{m'}-\underset{R^2}{\overset{R^1}{C}}-(C)_n-X-(C)_{n'}-\underset{R^6}{\overset{R^5}{C}}-(X^1)_{m''}-R^7 \quad (I)$$

wherein,
each of m, m' and m" is independently zero or one;
n is zero, one, two or three;
n' is zero, one or two;
R is hydrogen, lower alkyl, lower alkenyl, lower alkynyl, lower halo. alkyl, lower haloalkenyl, lower haloalkynyl, lower alkoxyalkyl, lower alkylthioalkyl, cycloalkyl, halocycloalkyl, cycloalkylalkyl, heterocycloalkyl, or heterocycloalkylalkyl;
each of $R^1$, $R^2$, $R^3$, $R^4$, $R^5$, $R^6$ and $R^8$ is independently hydrogen or lower alkyl;
$R^7$ is lower alkyl, lower alkenyl, lower alkynyl, lower haloalkyl, lower haloalkenyl, lower haloalkynyl, cycloalkyl, cycloalkylalkyl, phenyl or substituted phenyl; provided that when $X^1$ is $NR^9$, $R^7$ can also be selected from substituted or unsubstituted phenylthio and the group S—C(CH$_3$)$_2$—CN;
$R^9$ is hydrogen or selected from the values of $R^7$;
W is oxygen, sulfur, $NR^8$, $CR^3R^4$ or carbonyl;
$W^1$ is oxygen, sulfur, $NR^8$, $CR^3R^4$, carbonyl, sulfinyl, or sulfonyl;
X is oxygen, sulfur or $NR^8$;
X is oxygen, sulfur or $NR^9$;
Y is oxygen, sulfur or $NR^8$; and
Z is hydrogen, lower alkyl, lower haloalkyl or halogen.

A particular group of compounds for formula I comprises those of formula Ia $$R-(W^1)_m-\underset{Z}{\bigcirc}-(W)_{m'}-\underset{R^2}{\overset{R^1}{C}}-(C)_n-X-\overset{Y}{\overset{\|}{C}}-(X^1)_{m''}-R^7 \quad (Ia)$$

wherein
each of m, m' and m" is independently zero or one;
n is zero, one, two or three;
R is as defined above for formula I except for hydrogen, $R^7$ is as defined above for formula I whereby substituted phenyl is substituted at one, two or three of the ring carbon atoms by a group selected from C$_{1-8}$alkyls, C$_{1-8}$haloalkyl, C$_{1-8}$alkoxys, C$_{1-8}$haloalkoxy, halogen, nitro, cyano, and C$_{1-8}$alkylthio and the remaining substituents are as defined above for formula I;

The invention further relates to a method of controlling termites which comprises applying to the termites or their locus or to a locus where protection against termite infestation is desired an effective amount of a compound of formula II.

$$R-(W^1)_m-\underset{Z}{\bigcirc}-(W)_{m'}-\overset{R^1}{\underset{}{C}}H-(CH_2)_n-\overset{R^2}{\underset{}{C}}H-X-R^3 \quad (II)$$

each of m and m, is zero or one;
n is zero, one or two;
W is oxygen, sulfur, $NR^4$ or carbonyl;
$W^1$ is oxygen, sulfur, NP$_4$, carbonyl, sulfinyl or sulfonyl;
X is oxygen or sulfur;
Z is hydrogen, C$_{1-8}$alkyl, C$_{1-8}$haloalkyl or halogen;
R is C$_{1-8}$alkyl, C$_{1-8}$alkenyl, C$_{1-8}$alkynyl, C$_{1-8}$haloalkyl, C$_{2-8}$haloalkynyl, C$_{2-10}$alkoxyalkyl, C$_{2-10}$alkylthioalkyl, C$_{3-8}$cycloalkyl, C$_{3-8}$halocycloalkyl, C$_{4-12}$cycloalkylalkyl or heterocycloalkyl;
each of $R^1$ and $R^2$ is independently hydrogen or C$_{1-8}$alkyls
$R^2$ is hydrogen, C$_{1-8}$alkyl or halogen; and
either $R^3$ is an aromatic nitrogen-containing hetero-ring selected from pyridyl, 3-pyridazinyl, 2-pyrimidinyl, pyrazinyl, triazinyl or 2-thiazolyl which aromatic nitrogen-containing hetero-ring may be unsubstituted or substituted by one or more substituents selected from halogen, C$_{1-8}$alkyl, C$_{1-8}$haloalkyl, C$_{1-8}$alkoxy, C$_{1-8}$alkylthio and NO$_2$, or is a group (C$_1$):

$$\underset{R^{16}}{\overset{N}{\underset{}{\bigvee}}}\overset{S}{\underset{}{\bigvee}}\overset{R^{19}}{\underset{R^{17}}{\overset{(CH_2)_k}{\bigvee}}}R^{18} \quad (G_1)$$

in which k is zero or one; and
each of $R^{16}$, $R^{17}$, $R^{18}$ and $R^{19}$ is independently hydrogen or methyl.

A particular group of compounds of formula II ("Compounds IIa") comprises those wherein
each of m and m' is zero or one;
n is zero, one or two;
W is oxygen or sulfur;
$W^1$ is oxygen or sulfur;
X is oxygen or sulfur;
Z is hydrogen, lower alkyl of 1–5 carbons, lower haloalkyl of 1–5 carbons or halogen;
R is lower alkyl of 4–8 carbons, lower alkenyl of 4–8 carbons, or lower alkynyl of 4–8 carbons.,
$R^1$ is hydrogen or lower alkyl of 1–5 carbons;
$R^2$ is hydrogen, lower alkyl of 1–5 carbons or halogen; provided that when one of $R^1$ or $R^2$ is lower alkyl or halogen, the other of $R^1$ or $R^2$ is hydrogen,
$R^3$ is selected from one of the following groups:

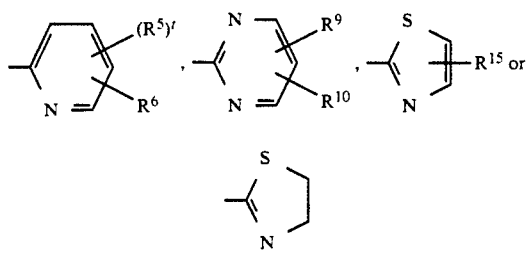

each of $R^5$, $R^6$, $R^9$, $R^{10}$ and $R^{15}$ is independently hydrogen, halogen, lower alkyl of 1-8 carbons, lower haloalkyl of 1-8 carbons, lower alkoxy of 1-8 carbons, lower alkylthio of 1-8 carbons or nitro; and t is one, two or three.

In the compound of formulae I and Ia those wherein
m, m' and m″=one
n'=zero
$W^1$ and Y are independently oxygen or sulfur
W is oxygen
Z=hydrogen
R=$C_{4-6}$ branched alkyl or alkenyl are preferred.

In the compounds of formulae II and IIa those wherein
m and m'=one
n=zero
$W^1$ is independently oxygen or sulfur
W is oxygen
Z=hydrogen
$R_3$ is an unsubstituted heterocyclic ring
$R_1$ and $R_2$ are independently hydrogen or methyl
R is $C_{4-6}$ branched alkyl or alkenyl are preferred.

The compounds of formula I, Ia, II and IIa, preferred groups and specific examples thereof, processes for their preparation, pesticidal formulations containing them and their use generally as insecticides and acaricides are described in U.S. application Ser. No. 07/368,465., EP Appln. No. 85810301.4; Publn. No. 169169, U.S. application Ser. No. 07/077,835; and EP Appln. No. 86810302.9; Publn. No. 218543 the contents of each of which are incorporated herein by reference.

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to six halogen atoms.

The term "lower alkenyl" refers to an alkenyl group, straight or branched, having a chain length of two to eight carbon atoms and one or two ethylenic bonds. The term "lower haloalkenyl" refers to a lower alkenyl group substituted with one to six halogen atoms.

The term "lower alkynyl" refers to an alkynyl group, straight or branched, having a chain length of two to eight carbon atoms and one or two acetilenic bonds. The term "lower haloalkynyl" refers to a lower alkynyl group substituted with one to six halogen atoms.

The term "lower alkoxyalkyl" refers to an alkyl group substituted at one of the carbon atoms by an alkoxy group, straight or branched, the total number of carbon atoms being not greater than ten.

The term "lower alkylthioalkyl" refers to a lower alkyl group substituted at one of the carbon atoms by an alkylthio group, straight or branched, the total number of carbon atoms being not greater than ten.

The term "cycloalkyl" refers to a cycloalkyl group of three to eight cyclic carbon atoms. The term "cycloalkylalkyl" refers to a cycloalkyl group wherein one hydrogen atom is replaced by a lower group, the total number of carbon atoms being from four to twelve. The term "halocycloalkyl" refers to a cycloalkyl group substituted with one to six halogen atoms.

The term "heterocycloalkyl" refers to a heterocycloalkyl group, saturated or unsaturated, of two to six carbon atoms and one to three atoms selected from nitrogen, oxygen or sulfur. The term "heterocycloalkylalkyl" refers to a heterocycloalkyl group wherein one hydrogen is replaced by a lower alkyl group, the total number of carbon atoms being from three to twelve.

The term "substituted phenyl" or "phenylthio" refers to a phenyl or phenylth2io group substituted at one, two or three of the ring carbon atoms with a group selected from lower alkyl, lower haloalkyl, lower alkoxy, lower haloalkoxy, halogen,. nitro, cyano and lower alkylthio.

The individual compounds shown below in Tables I and II are preferred with compounds 2, 6 and 8 being particularly preferred.

TABLE I

| (Compounds II: $W = W^1 = 0$; $m = m' = 1$; $n = 0$; $Z = H$) | | | | |
|---|---|---|---|---|
| R | $R_1$ | $R_2$ | X | $R_3$ |
| 1 CH₃CH₂CH—CH₃ | H | CH₃ | O | 2-pyridyl |
| 2 CH₃CH₂CH—CH₃ | H | H | O | 2-pyridyl |
| 3 CH₃CH₂CH—CH₃ | H | H | O | 2-thiazolyl |
| 4 CH₃CH₂CH—CH₃ | H | CH₃ | O | 2-thiazolyl |
| 5 CH₃CH₂CH CH₃ | H | H | S | 2-thiazolinyl |

TABLE II

| (Compounds Ia; $W = 0$; $m = m' = m'' = n = 1$; $Z = H$) | | | | | | | | | |
|---|---|---|---|---|---|---|---|---|---|
| R | $W^1$ | $R_1$ | $R_2$ | $R_3$ | $R_4$ | X | Y | $X^1$ | $R_7$ |
| 6 CH₃CH₂CH—CH₃ | O | H | H | H | H | NH | O | O | C₂H₅ |
| 7 CH₃CH₂CH—CH₃ | O | H | H | H | H | O | O | NH | C₂H₅ |
| 8 CH₃CH₂CH—CH₃ | S | H | H | H | H | NH | O | S | C₂H₅ |
| 9 CH₃CH₂CH—CH₃ | O | CH₃ | H | H | H | NH | O | O | C₂H₅ |
| 10 CH₃CH₂CH—CH₃ | O | H | H | H | H | O | S | NC₂H₅ | C₂H₅ |
| 11 CH₃C=CHCH₂ CH₃ | O | H | H | H | H | O | O | NH | i-C₃H₇ |

In the use of compounds of the invention for combatting termites, they may conveniently be combined with a suitable carrier substance or substances for application to the termites or their habitat. The carrier can be liquid or solid and include adjuvants such as wetting agents, dispersing agents and other surface active agents. The compounds can be used in formulations such as baits, solutions, dusts, granules, emulsifiable concentrates, sprayables and the like. Suitable solid carriers include natural and synthetic silicates and clays, carbon or charcoal granules, natural and synthetic resins, waxes and the like. Suitable liquid carriers include water, aromatic hydrocarbons, alcohols, vegetable and mineral oils, ketones, and the like.

The compounds of the invention can be combined with cyclodextrin to make a cyclodextrin inclusion complex for application to the termites or their habitat.

For soil application granular formulations of baits may be used in which the active ingredient is coated or impregnated on granules of, for example, corn cobs, gypsum, pumice or charcoal. The impregnated granules may be coated with a polymer such as, for example, a resin or a wax to regulate the rate of release of the active ingredient.

Soil spray formulations may also be employed.

Microencapsulated forms may also be mentioned where exceptionally long control is required (cf e.g. USPs).

A particularly important use for compounds of the invention is in protecting wood against termite attack. In view of their favorable soil stability, the compounds are useful in the protection of above and underground wooden parts of houses. The protection of wood can be effected directly or indirectly using a termite-controlling amount of a compound of the invention. Direct protection of wood can, for example, be achieved by impregnation, spray or perforation application., indirect protection, for example, by application to the termite infested area surrounding the wood to be protected. When the wood to be protected is a wood basement, the indirect protection can be achieved by incorporation into or application onto the soil surrounding the basement parts.

In general, the application form for direct as well as indirect wood protection, will conveniently be a diluted form or as a solid bait comprising from e.g. 0.01 to 10%, especially 0.01 to 1% e.g. 1% by weight of active ingredient.

For direct protection of the wood, the application form will be suitably an oil formulation, for indirect protection the application form is suitably a diluted emulsion concentrate. The amount to be applied will depend on various factors such as method and conditions of application, and can be easily established by routine experiments by persons skilled in the art.

Where protection is intended by direct spray application of active ingredient onto the wood surface, satisfactory protection will, in general, be obtained by applying from 0.5 to 5.0 g (a.i.) e.g. 100 to 200 ml of a 1% by weight oil application form thereof, per square meter of wood surface. Such spray application may be repeated whenever necessary. Where the compound is applied by the so-called perforation technique, involving the injection of a suitable formulation under (preferably high) pressure through the small holes of wood perforated forthat particular purpose, the amount to be applied will conveniently be in the range of 500 to 600 liters of 1% by weight active ingredient application form, i.e. 5.0 to 6.0 kg of active ingredient per ms of wood. Impregnation of the wood for protective purposes can be effected using appropriate liquid application forms in known impregnation techniques.

Where indirect wood protection is desired, the active ingredient can for example be incorporated into the soil at both sides of the basement frame.

This, for example, can be done by digging small ditches, e.g. of 15–30 cm breadth and 20–30 cm depth, along the basement frame, admixing said removed soil with a suitable amount of active ingredient, filling the ditches with the treated soil and applying of the filled ditches. Where a 1% weight application form is used, satisfactory results will, in general, be obtained by admixing 1 to 5 liters of said application form with the amount of soil (0.03 to 0.1 m$^3$) dug up per running meter of the above-mentioned ditches (i.e. 100 to 1500 g of active ingredient per m$^3$ of soil). A suitable additional amount of active ingredient conveniently applied onto the surface of the ditches filled with treated soil is for example 0.5 to 1 litre of a 1% application form of active ingredient per square meter of removed soil surface.

Alternatively, the active ingredient may be incorporated into materials of the type used by termites in feeding and nest building and thus can be transported back to the nest enabling the termites to be combatted "at source". Examples of such material are cellulose materials e.g. cardboard, paperboard, wood dust, wood cubes, cellulose powder, cotton wool and other cellulose based materials. Suitable application rates would be 1 to 100 mg/g dry cellulose based material or 0.1 to 10 mg/g of hydrated material.

Such an approach is particularly successful given the effect of the compounds of the invention is inducing young termites to become presoldier or soldier termites which do not attack wood and can only subsist on predigested wood provided by worker termites. This disruption of the social structure within the termite colony (by formation of excess soldiers and presoldiers) rapidly leads to decimation of the population by cannibilization and inability to expand or provide food (paucity of workers). (cf J. Econ. Entomol. v. 78 no. 6 1259ff; J. Econ. Entomol. v. 82 no. 5 1370ff; Annals. Entomol. Sco. Am. v. 72 no. 4 p. 503 ff.)

For this approach formulation as baits is particularly useful especially if bait enhancers such as synthetic trail pheromones and wood previously invaded by dry-rot fungi are employed. For examples of such baits cf. e.g. PEST CONTROL TECHNOLOGY, March 1985 p. 38ff; J. Econ. Entomol. v. 77 no. 5 p. 1986ff).

It will be appreciated that for application form comprising more of less than 1% by weight of active ingredient the volume to be applied should be adapted accordingly.

The method of invention is particularly effective against subterranean termites such as *Reticulitermes virginicus, Reticulitermes speratus* (Kolbe), *Coptotermes formosanus* (Shiraki), *Cryptotermes domesticus* (Haviland), *Incisistermes minor* (Hagen) and *Zootermopsis augusticollis* (Hagen).

The active ingredient can alternatively be incorporated in usually fibrous material used to form barriers in the soil surrounding wooden structures.

Formulations are prepared having the following compositions, percent by weight.

| A. Emulsifiable concentrate: | |
|---|---|
| Compound No. 6 | 50.4 |
| Toximol RHF | 6.4 |
| Toximol S | 1.6 |
| Tenneco 500/100 | 41.6 |

Toximol RHF is an anionic-nonionic blend emulsifier. Toximol S is a nonionic-anionic blend emulsifier. Tenneco 500/100 is trimethylbenzene.

| B. Granule: | |
|---|---|
| Compound No. 8 | 5.6 |
| AGSORB RVM 20/40 | 93.4 |
| Dipropylene glycol | 1.0 |

Agsorb RVM 20/40 is montmorillonite, regular volatile material, 20/40 mesh.

| C. Baits: | |
|---|---|
| | % |
| (i) Sawdust composites | |
| a) Compound No. 6 | 0.1 |
| Sawdust | 20.0 |
| Agar | 1.0 |
| Water | 78.9 |
| b) Compound No. 6 | 0.5 |
| Sawdust | 94.5 |
| Agar | 5.0 |
| (ii) Baitblocks (after solvent evaporation) | |
| Compound No. 6 | 0.1 |
| Wood | 99.9 |
| (iii) Paper products (after solvent evaporation) | |
| Compound No. 6 | 0.1 |
| Paper | 99.9 |

Each of the above baits may optionally be enhanced with a synthetic trial pheromone at a concentration of e.g. 0.01% or less.

Biological Data

A. Active substances are fed to *Reticulitermes virginicus* workers (25 per replicate) at various concentrations on α-cellulose on a wt/wt basis.

Of the 25 termites in each of 3 replicates the maximum number of presoldiers in one replicate during weeks 3 and 4 is as follows

| Concentration | Cmpd. 6 | | Cmpd. 8 | | Cmpd. 2 | |
|---|---|---|---|---|---|---|
| (ppm) | 3 wk | 4 wk | 3 wk | 4 wk | 3 wk | 4 wk |
| 100 | 0 | 0 | 1 | 0 | 9 | 11 |
| 500 | 6 | 5 | 5 | 5 | 11 | 11 |
| 1,000 | 11 | 14 | 10 | 3 | 18 | 19 |
| 2,500 | 9 | 13 | 8 | 1 | 4 | 4 |
| 5,000 | 3 | 4 | 1 | 0 | 7 | dead |

B. Active substances are incorporated at various concentrations in a bait formation as described in example C(i)(a) above. Bait is placed in small containers each containing 10 larvae (nymphs) of Zootermopsis augusticollis (2 replication/dosage rate). Employing Compound No. 6 at a concentration of 100 ppm 95% of the nymphs has turned into soldiers by day 20.

What is claimed is:

1. A method for controlling termites which comprises applying to the termites, their locus or a locus where protection against termite infestation is desired an effective amount of a compound of the following formula I

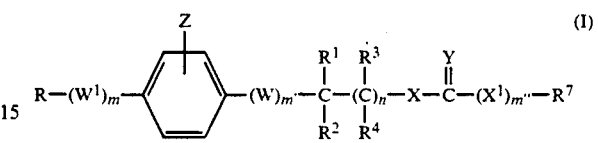

wherein
each of m, m' and m" is one;
n is zero, one, two or three;
R is hydrogen, lower alkenyl, lower alkynyl, lower halogenalkyl, lower haloalkenyl, lower haloalkynyl, lower alkoxyalkyl, lower alkylthioalkyl, cycloalkyl or cycloalkylalkyl;
each of $R^1$, $R^2$, $R^3$, $R^4$ and $R^8$ is independently hydrogen or lower alkyl;
$R^7$ is lower alkyl, lower alkenyl, lower alkynyl, lower haloalkyl, lower haloalkenyl, lower haloalkynyl, cycloalkyl or cycloalkylalkyl;
W is oxygen or sulfur;
$W^1$ is oxygen or sulfur;
X is $NR^8$;
$X^1$ is oxygen or sulfur;
Y is oxygen or sulfur; and
Z is hydrogen, lower alkyl, lower haloalkyl or halogen.

2. The method according to claim 1 whereby in the compound of formula m, m', m" and n are each one, $W^1$ and Y are independently oxygen or sulfur, W is oxygen and Z is hydrogen.

3. The method according to claim 1 whereby a compound of formula I is employed wherein R is $C_4$–$C_8$ branched chain alkyl or alkenyl.

4. The method according to claim 1 whereby a compound of formula I is employed wherein W is oxygen, m, m', m" and n are one, Z is hydrogen, $W^1$ is oxygen or sulfur, $R^1$ is hydrogen or methyl, $R^2$, $R^3$, $R^4$ are hydrogen, X is NH, Y is oxygen or sulfur, $X^1$ is oxygen or sulfur and $R^7$ is ethyl or isopropyl.

5. The method according to claim 1 whereby a compound of formula I is employed wherein W is oxygen, m, m', m" and n are one, Z is hydrogen, $W^1$ is oxygen, $R^1$, $R^2$, $R^3$ and $R^4$ are hydrogen, X is NH, Y and $X^1$ are oxygen, $R^7$ is ethyl and R is sec-butyl.

6. The method according to claim 1 whereby a compound of formula I is employed wherein W is oxygen, m, m', m" and n are one, Z is hydrogen, $W^1$ is sulfur, $R^1$, $R^2$, $R^3$ and $R^4$ are hydrogen, X is NH, Y is oxygen, $X^1$ is sulfur, $R^7$ is ethyl and R is sec-butyl.

* * * * *